United States Patent [19]

Gerber et al.

[11] 4,055,765
[45] Oct. 25, 1977

[54] GAMMA CAMERA SYSTEM WITH COMPOSITE SOLID STATE DETECTOR

[75] Inventors: Mark S. Gerber, Columbus; Don W. Miller, Westerville, both of Ohio

[73] Assignee: The Ohio State University, Columbus, Ohio

[21] Appl. No.: 680,755

[22] Filed: Apr. 27, 1976

[51] Int. Cl.² ............................................. G01T 1/22
[52] U.S. Cl. ................................ 250/370; 250/363 S
[58] Field of Search ..................... 250/363 S, 370, 385

[56] References Cited

U.S. PATENT DOCUMENTS

| | | | |
|---|---|---|---|
| 3,812,360 | 5/1974 | Tkyva | 250/370 |
| 3,812,361 | 5/1974 | Prag et al. | 250/370 |
| 3,891,851 | 6/1975 | Fletcher et al. | 250/385 |

Primary Examiner—Davis L. Willis
Attorney, Agent, or Firm—Sidney W. Millard

[57] ABSTRACT

A composite solid-state detector for utilization within gamma cameras and the like. The detector's formed of an array of detector crystals, the opposed surfaces of each of which are formed incorporating an impedance-derived configuration for determining one coordinate of the location of discrete impinging photons upon the detector. A combined read-out for all detectors within the composite array thereof is achieved through a row and column interconnection of the impedance configurations. Utilizing the noted read-outs for respective sides of the discrete crystals, a resultant time-constant characteristic for the composite detector crystal array remains essentially that of individual crystal detectors.

22 Claims, 7 Drawing Figures

GAMMA CAMERA SYSTEM WITH COMPOSITE SOLID STATE DETECTOR

BACKGROUND

The field of nuclear medicine has long been concerned with techniques of diagnosis wherein radio pharmaceuticals are introduced into a patient and the resultant distribution or concentration thereof as evidenced by gamma ray intensities is observed or tracked by an appropriate system of detection. An important advantage of the diagnostic procedure is that it permits non-invasive investigation of a variety of conditions of medical interest. Approaches to this investigative technique have evolved from early pioneer procedures wherein a hand-held radiation counter was utilized to map body contained areas of radioactivity, to more current systems for imaging gamma ray source distributions, in vivo utilizing stationary cameras with broadened fields of view. In initially introduced practical systems, scanning methods were provided for generating images, such techniques generally utilizing a scintillation-type gamma ray detector equipped with a focusing collimator which moved continuously in selected coordinate directions, as in a series of parallel sweeps, to scan regions of interest. A drawback to the scanning technique resides in the necessarily longer exposure times required for the derivation of an image. For instance, such time elements involved in image development generally are overly lengthy to carry out dynamic studies of organ function.

By comparison to the rectilinear scanner described above, the later developed "gamma camera" is a stationary arrangement wherein an entire region of interest is imaged at once. As initially introduced, the stationary camera systems generally utilized a larger diameter sodium Iodide, Na I (TI) crystal as a detector in combination with a matrix of photomultiplier tubes. For additional information concerning such a camera, see:

I. Anger, H.O., "A New Instrument For Mapping Gamma Ray Emitters", *Biology and Medicine Quarterly Report* UCRL— 3653, 1957.

A multiple channel collimator is interposed intermediate the source containing subject of investigation and the scintillation detector crystal. When a gamma ray emanating from the region of investigative interest interacts with the crystal, a scintillation is produced at the point of gamma ray absorption and appropriate ones of the photomultiplier tubes of the matrix respond to the thus generated light to develop output signals. The original position of gamma ray emanation is determined by position responsive networks associated with the outputs of the matrix.

A continually sought goal in the performance of gamma cameras is that of achieving a high resolution quality in any resultant image. Particularly, it is desirable to achieve this resolution in combination with concomitant utilization of a highly versatile radionuclide or radiolabel, such as 99m-Technetium, having a gamma ray or photon energy in the region of 140 keV.

The resolution capabilities of gamma cameras incorporating scintillation detector crystals, inter alia, is limited both by the light coupling intermediate the detector and phototube matrix or array as well as by scatter phenomena of the gamma radiation witnessed emanating from within the in vivo region of investigation. Concerning the latter scattering phenomena, a degradation or resolution occurs from scattered photons which are recorded in the image of interest. Such photons may derived from Compton scattering into trajectories wherein they are caused to pass through the camera collimator and interact photoelectrically with the crystal detector at positions other than their point of in vivo derivation. Should such photon energy loss to the Compton interaction be less than the energy resolution of the system, it will effect an off-axis recordation in the image of the system as a photopeak photon representing false information. As such scattered photons record photopeak events, the false information and consequent resoltuion quality of the camera diminishes. For the noted desirable 140 keV photons, the scintillation detector-type camera energy resolution is approximately 22 keV. With this resolution, photons which scatter through an angle from 0° to about 70°, which pass through the collimator, will be seen by the system as such photopeak events.

A continuing interest in improving the resolution qualities of gamma cameras has lead to somewhat extensive investigation into imaging systems incorporating relatively large area solid-state semiconductor detectors. Such interest has been generated principally in view of theoretical indications of an order of magnitude improvement in statistically limited resolution to provide significant improvements in image quality. In this regard, for example, reference may be made to the following publications:

II. R. N. Beck, L. T. Zimmer, D. B. Charleston, P. B. Hoffer, and N. Lembares, "The Theoretical Advantages of Eliminating Scatter in Imaging Systems," *Semiconductor Detectors in Nuclear Medicine*, (P. B. Hoffer, R. N. Beck, and A. Gottschalk, editors), Society of Nuclear Medicine, New York, 1971, pp. 92–113.

III. R. N. Beck, M. W. Schuh, T. D. Cohen, and N. Lembares, "Effects of Scattered Radiation on Scintillation Detector Response", "*Medical Radioisotope Scintigraphy*", IAEA, Vienna, 1969, Vol. 1, pp. 595–616.

IV A. B. Brill, J. A. Patton, and R. J. Baglan, "An Experimental Comparison of Scintillation and Semiconductor Detectors for Isotope Imaging and Counting", *IEEE Trans. Nuc. Sci.*, Vol. NS-19, No. 3, pp. 179–190, 1972.

V. M. M. Dresser, G. F. Knoll, "Results of Scatting in Radioisotope Imaging", *IEEE Trans. Nuc. Sci., Vol. NS*-20, No. 1, pp. 266–270, 1973.

Particular interest on a part of investigators has been paid to detectors formed as hybridized diode structures fashioned basically of germanium. To provide discrete regions for spatial resolution of impinging radiation, the opposed parallel surfaces of the detector diodes may be grooved or similarly configured to define transversely disposed rows and columns, thereby providing identifiable discrete regions of radiation response. Concerning such approaches to treating the detectors, mention may be made of the following publications:

VI. J. Detko, "Semiconductor Diode Matrix for Isotope Localization", *Phys. Med. Biol.*, Vol. 14, No. 2, pp. 245–253, 1969.

VII. J. F. Detko, "A Prototype, Ultra Pure Germanium Orthogonal Strip Gamma Camera", *Proceedings of the IAEA Symposium on Radioisotope Scintigraphy*, IAEA/SM-164/135, Monte Carlo, October 1972.

VIII R. P. Parker, E. M. Gunnerson, J. L. Wankling, and R. Ellis, "A Semiconductor Gamma Camera with Quantitative Output" *Medical Radioisotope Scintigraphy.*

IX. V. R. McCready, R. P. Parker, E. M. Gunnerson, R. Ellis, E. Moss, W. G. Gore, and J. Bell, "Clinical Tests on a Prototype Semiconductor Gamma-Camera", *British Journal of Radiology*, Vol. 44 58–62, 1971.

X. Parker, R. P., E. M. Gunnerson, J. S. Wankling, R. Ellis, "A Semiconductor Gamma Camera with Quantitative Output", *Medical Radioisotope Scintigraphy*, Vol. 1, IAEA, 1969, p. 71.

XI. Detko, J. F., "A Prototype, Ultra-Pure Germanium, orthogonal-Strip Gamma Camera", *Medical Radioisotope Scintigraphy*, Vol. 1, Vienna, IAEA, 1973, p. 241.

XII. Schlosser, P. A., D. W. Miller, M. S. Gerber, R. F. Redmond, J. W. Harpster, W. J. Collis, W. W. Hunter, Jr., "A Practical Gamma Ray Camera System Using High Purity Germanium", presented at the 1973 IEEE Nuclear Science Symposium, San Francisco, November 1973; also published in *IEEE Trans. Nucl. Sci.*, Vol. NS-21, No. 1 February 1974, p. 658.

XIII. Owen, R. B., M. L. Awock, "One and Two Dimensional Position Sensing Semiconductor Detectors," *IEEE Trans. Nucl. Sci.*, Vol. NS-15, June 1968, p. 290.

In the more recent past, investigators have shown particular interest in forming orthogonal strip matrix detectors from p-i-n semiconductors fashioned from an ultra pure germanium material. In this regard, reference is made to U.S. Pat. No. 3,761,711 as well as to the following publications:

XIV. J. F. Detko, "A Prototype, Ultra Pure Germanium, Orthogonal Strip Gamma Camera," *Proceedings of the IAEA Symposium on Radioisotope Scintigraphy*, IAEA/SM-164/135, Monte Carlo, October, 1972.

XV. Schlosser, P. A., D. W. Miller, M. S. Gerber, R. F. Redmond, J. W. Harpster, W. J. Collis, W. W. Hunter, Jr., "A Practical Gamma Ray Camera System Using High Purity Germanium," presented at the 1973 IEEE Nuclear Science Symposium, San Francisco, November 1973; also published in *IEEE Trans. Nucl. Sci.*, Vol. NS-21, No. 1, February 1974, p. 658.

High purity germanium detectors promise advantages in gamma camera resolution and consequent diagnostic flexibility. For instance, by utilizing high purity germanium as a detector, lithium drifting arrangements and the like for reducing impurity concentrations are avoided and the detector need only be cooled to requisite low temperatures during its clinical operation. Readout from the orthogonal strip germanium detectors is described as being carried out utilizing a number of techniques, for instance, each strip of the detector may be connected to a preamplifier-amplifier channel and thence directed to an appropriate logic function and visual readout. In another arrangement, a delay line readout system is suggested with the intent of reducing the number of preamplifier-amplifier channels, and a technique of particular interest utilizes a charge splitting method. With this method or technique, position sensitivity is obtained by connecting each contact strip of the detector to a charge dividing impedance network. Each end of each network is connected to a virtual earth, charge sensitive preamplifier. When a gamma ray interacts with the detector, the charge release enters the string of resistors or area of impedance and divides in relation to the amount of resistance between its entry point in the string and the preamplifiers at the network output. Utilizing fewer preamplifiers, the cost and complexity of such systems is advantageously reduced. A more detailed description of this readout arrangement is provided in:

XVI. Gerber, M. S., Miller, D. N., Gillespie, B., and Chemistruck, R. S., "Instrumentation For a High Purity Germanium Position Sensing Gamma Ray Detector," *IEEE Trans. on Nucl. Sci.*, Vol. NS-22, No. 1, February, 1975, p. 416.

To achieve requisite performance and camera image resolution, it is neccassary that substantially all sources of noise be minimized and that false information within the system be accounted for. In the absence of adequate noise resolution, the performance of the imaging systems may be compromised to the point of impracticality. Until the more recent past, charge-splitting germanium detector arrangements have not been considered to be useful in gamma camera applications in consequence of thermal noise anticipated in the above-noted resistor-divider networks, see publication VII, supra. However, such noise centered considerations now are accommodated for within camera system designs. In this regard, reference is made to copending application for U.S. patent, Ser. No. 656,304 by P. A. Schlosser et al, filed Feb. 9, 1976, entitled "Gamma Ray Camera for Nuclear Medicine": and application Ser. No. 680,754 by O. Miller et al. entitled "Control System for Gamma Camera" filed Apr. 7, 1976, both applications being assigned in common herewith.

Another aspect in the optimization of resolution of the images of gamma cameras resides in the necessarily inverse relationship between resolution and sensitivity. A variety of investigations has been conducted concerning this aspect of camera design, it being opined that photon noise limitations, i.e. statistical fluctuations in the image, set a lower limit to spacial resolution Further, it has been pointed out that the decrease in sensitivity witnessed in conventional high resolution collimators may cancel out any improvements sought to be gained in image resolution. A more detailed discourse concerning these aspects of design are provided, for instance, in the following publications:

XVII. E. L. Keller and J. W. Coltman, "Modulation Transfer and Scintillation Limitations in Gamma Ray Imaging," *J. Nucl. Med.* 9, 10, 537–545 (1968).

XVIII. B. Westerman, R. R. Sharma, and J. F. Fowler, "Relative Importance of Resolution and Sensitivity in Tumor Detection," *J. Nucl. Med.* 9, 12, 638–640 (1968).

More recent investigation of gamma camera performance has identified still another operational phenomenum tending to derogate from spatial resolution quality. This phenomenon is referred to as "aliasing" and represents a natural outgrowth of the geometry of the earlier noted orthogonal strip germanium detector. A more detailed discussion of the phenomena is provided at:

XIX. J. W. Steidley, et al., "The Spatial Frequency Response of Orthogonal Strip Detectors, " *IEEE Trans. Nuc. Sci., February,* 1976.

To remain practical, it is necessary that the imaging geometry of stationary type gamma cameras provide for as large a field of view as is practical. More particularly, considerations of clinical practicality require a camera field of view large enough to encompass the entire or a significant extent of the profiles of various organs of interest. Because of the considerable limitations encountered in the manufacture of detector crystals, for instance, high purity germanium crystals, the size of solid state detector components components necessarily is limited. As a consequence, composite detector configurations are required which conjoin a plurality of smaller detector components to provide an imaging field of view or radiation acceptance geometry of effectively larger size. However, such a union of a multitude of detector components must be carried out in such a manner that no significant loss of validity and acuity in the final image generated by the camera system. For instance, in the latter regard, spatial information must have a consistency of meaning across the entire extend of an ultimately displayed image of an organ, otherwise, clinical evaluation of such images may be encumbered considerally.

SUMMARY

The present invention is addressed to an improved gamma camera system and detector arrangement related thereto. Advantageously utilizing solid state detector components, a composite geometry for a camera detector unit is evolved to permit the fabrication of gamma cameras having fields of view suited for practical clinical applications.

While being characterized as a composite assembly of solid state detector components fabricable commensurately with the current state of the art, the overall detector arrangement advantageously permits informational signal readout under conditions wherein the time constant characteristic for the detector function remain at advantageously optimum values.

Another feature and object of the invention is to provide a gamma camera system including a composite solid state detector for use in the idenfication of the distribution of radiation eminating from a source containing region of interest which comprises a plurality of adjacently disposed solid-state detector components. Formed, for instance. of germanium or the like each of the adjacently disposed detector components is configured having a surface arranged for exposure for impinging radiation and exhibits discrete interactions therewith at given spatially definable locations. That surface of the detector component and the surface disposed opposite thereto and parallel therewith are associated with an impedance readout arrangement which provides for impedances defined output signals relating the location of the noted interaction with at least one spatial coordinate parameter of a selected directional sense within the array of discrete detector components. Further, the detector components are arranged to exhibit rows and columns of the noted interaction with at least one spatial coordinate parameter of all of the surfaces within such row or column are mutually parallel in alignment. The composite detector further incorporates means interconnecting at least two of the outputs of such surfaces within a given row or column for collecting the impedance defined signals or charges as are derived therefrom. Preferably, the collection of this information is made in a parallel circuit scheme to provide a minimization of the effective capacitance of the entire detector assembly.

As another object and aspect of the invention, the opposed surfaces of a discrete detector component within a composite detector are configured to define arrays of mutually parallel strips each of these strips having a discrete area of influence over the occurrence of an interaction of the detector with impinging radiation. The impedance-type charge treating arrangement for each of these surfaces is present as an impedance network, for instance a chain of discrete resistor elements associated along the extent of the strip array. The output of this chain is coupled in parallel circuit relationship with a next adjacent surface impedance network within a row or column alignment of the detector, this row or column being aligned in the spatial coordinate directional sense predesignated therefore. In a preferred embodiment, the opposed surfaces of the discrete detector components within a composite detector assembly are arranged to record spatial information in a mutually orthogonally disposed coordinate sense.

Another aspect and object of the invention is to provide a composite detector assembly incorporating individual detector components, the surfaces of which are formed incorporating a readout impedance system present as a layer or surface region of predetermined resistance and disposed between two contact readout strips. Such region provides an impedance structure wherein a proportionality of charge distribution between the contact strips is examined by circuit readout arrangements to derive coordinate-labeled signals representing spatial information for a gamma camera imaging system. To assure appropriate image integrity between that subject of clinical interest imaged by the detector structure and the ultimate gamma camera system readout, the areas of the discrete detector components within a composite detector as they are intended to recieve radiation impinging from the subject, are formed having equivalent surface areas. As a consequence, no significant distortion in the image ultimately perceived by the system operator is generated.

Another object of the invention is to provide a composite solid state detector formed of discrete detector components each of which is formed having discrete adjacent parallel and substantially mutually electrically isolated strip regions both upon the surface intended to receive impinging radiations and the surface opposite thereto. These groupings of parallel strip regions are mutually orthogonally disposed with respect to each other with each side of a component and the components are arranged in mutual adjacency so that the strip regions of a given component surface are alligned in parallel with those regions of an adjacent component to define groupings described herein as "rows and columns". In one embodiment, the adjacent strip regions are correspondingly adjacent component surfaces are electrically interconnected in series relationship and such serially connected strip regions are provided discrete outputs for each grouping. Impedance means and, preferably in the form of a charge splitting resistor chain is associated with the outputs of each grouping to provide impedance defined signals which relate the location of an interaction of impinging radiation with the coordinate direction of the appropriately influenced strip region and the relative position of the interconnected strip region within a grouping.

Other objects of the invention will, in part, be obvious and will, in part, appear hereinafter.

The invention, accordingly, comprises the system and apparatus possessing the construction, combination of elements and arrangement of parts which are exemplified by the following detailed disclosure.

For a fuller understanding of the nature and objects of the invention, reference should be had to the following

DETAILED DESCRIPTION

Figure 1:
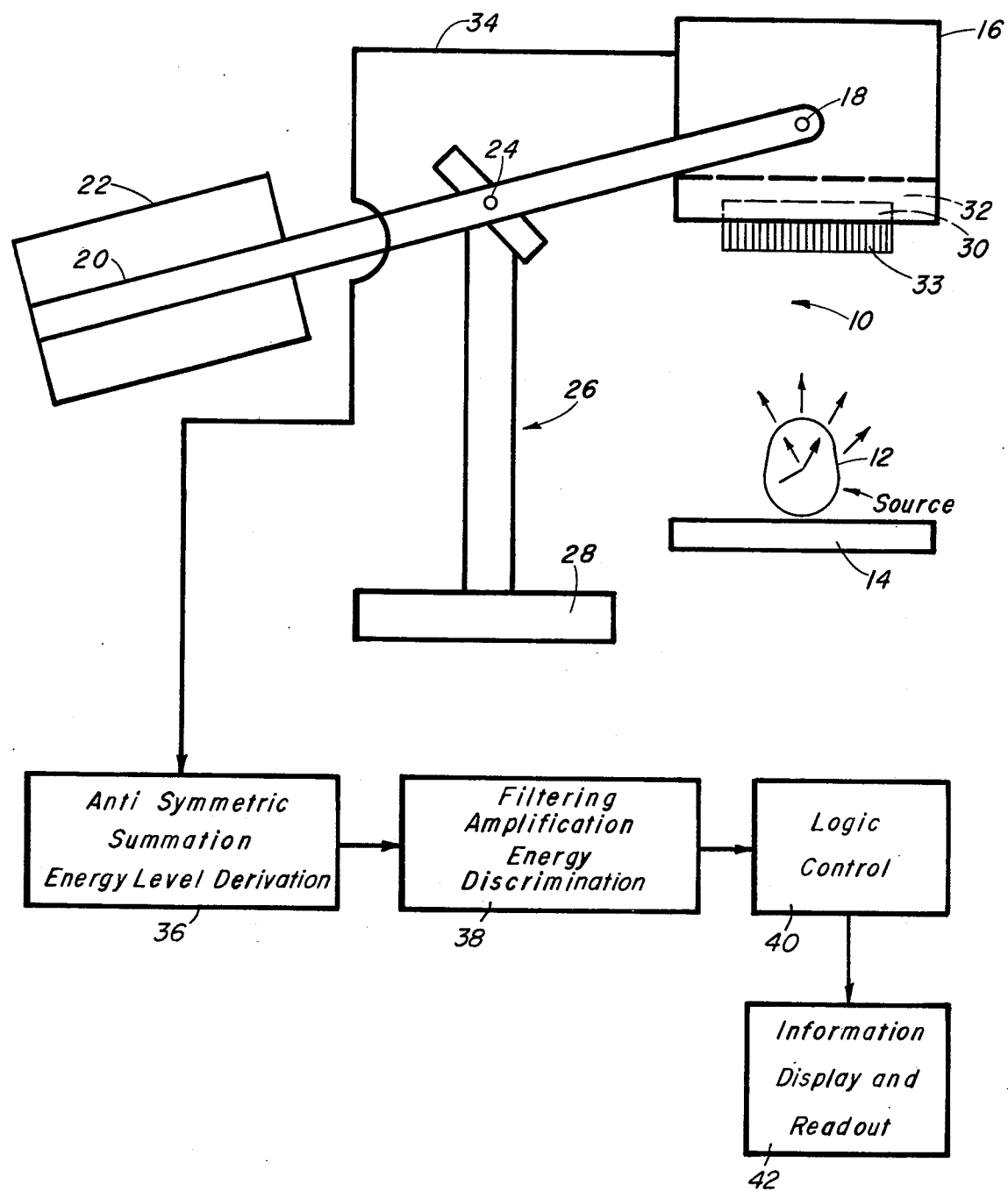
FIG. 1 is a schematic representation of gamma camera arrangement as may utilize the improvements of the invention, showing, in block schematic form, control functions of the system.

As indicated in the foregoing discourse, during contemplated clinical utilization, a gamma camera arrangement according to the instant invention is used to image gamma radiation eminating from a region of radiopharmaceutical source distribution within a patient. Looking to FIG. 1, an exaggerated schematic representation of such a clinical environment is revealed generally at 10. The environment 10 schematically shows the cranial region 12 of a patient to whom has been administered a radiolabeled pharmaceutical, which pharmaceutical will have tended to concentrate within a region of investigative interest. Accordingly, radiation is depicted as eminating from this region 12 as the patient is positioned beneath the head or housing 16 of a gamma camera. Housing 16 is pivotally supported at 18 from a beam 20. Beam 20, carrying a counter-weight 22, is pivotally supported at 24 in dual axis gimbal fashion from an upstanding support 26. Support 26 is fixedly attached to and extends from a base member 28. As is represented only in dotted line and generalized fashion, the head 16 is configured to retain an ultra-pure germanium orthogonal strip type semi-conductor detector 30 as well as resistor-divider networks tapping the detector and preamplification stages (not shown in FIG. 1) within a vacuum chamber 32. Chamber 32 is retained at a predetermined low temperature, for instance 77° K by an appropriate cryogenic system during operation of the head 16 to provide one aspect of necessary detector and electrode noise diminuation. Adjacent to the detector 30 and disposed intermediate the detector and the patient-retained source of radiation 12, is a multi-channel collimator 33, the design and structure of which is described in detail in the above-referenced application for U.S. patent Ser. No. 656,304.

During the operation of the gamma camera, radiation emunating from source 12 is spatially coded initially at collimator 33 by attenuating or rejecting off-axis radiation representing false image information. That radiation passing collimator 33 impinges upon detector 30 and a significant portion thereof is converted to discrete charges or image signals. Detector 30 is so configured as to distribute these signals to resistor chains as well as select preamplification stages retained within chamber 32 to provide initial signals representative of image spatial infromation along conventional coordinate axes as well as representing values for radiation energy levels. This data then is introduced, as represented schematically by line 34, to filtering and logic circuitry which operates thereupon to derive an image of optimized resolution and veracity. In the latter regard, for instance, it is desired that only true image information be elicited from the organ being imaged. Ideally, such information should approach the theoretical imaging accuracy of the camera system as derived, for instance, from the geometry of the detector structure 30 and collimator arrangement 33 as well as the limitations of the electronic filtering and control of the system. Instrumentation for achieving the latter function is described, for instance, in detail and the following publication which is incorporated herein by reference:

XX. Gerber, M. S., Miller, D. W., Gillespie, B., and Chemistruck, R. S., "Instrumentation for a High Purity Germanium Position Sensing Gamma Ray Detector," IEEE Trans. on Nucl. Sci., Vol. NS-22, No. 1, February 1975, p. 416.

Image spatial and energy level signals from line 34 initially, are introduced into Anti-Symmetric Summation and Energy Level Derivation represented at block 36. As is described in more detail later herein, the summation carried out at block 36 operates upon the charges directed into the resistive chains or networks associated with the orthogonal logic structuring of detector 30 to derive discrete signals or charge values corresponding with image element location. Additionally, circuitry of the function of block 36 derives a corresponding signal representing the energy levels of the spatial information. The output of block 36 is directed to Filtering Amplification and Energy Discrimination functions as are represented at block 38. Controlled from a Logic Control function shown at block 40, function 38 operates upon the signal input thereto to accommodate the system to parallel and serially defined noise components through the use of Gaussian amplification or shaping, including trapezoidal pulse shaping of data representing the spatial location of image signals. Other methods, such as delay line filtering, of course, may provice this function. Similarly, the energy levels of incoming signals are evaluated, for instance, utilizing single channel analyzer components controlled by logic 40 to establish an energy level window for data received within the system. In this regard, signals evaluated, for instance, utilizing single channel analyzer components controlled by logic 40 to establish an energy level window for data received within the system. In this regard, signals falling above and below predetermined energy levels are considered false and are blocked. From Amplification and Discrimination stage 38 and Logic Control 40, the analyzed signals are directed into an Information Display and Readout Function, as is represented at block 42. Components within function block 42 will include display screens of various configurations, image recording devices, for instance, photographic apparatus of the instant developing variety, radiation readout devices and the like, which are controlled at the option of the system operator.

Figure 2:
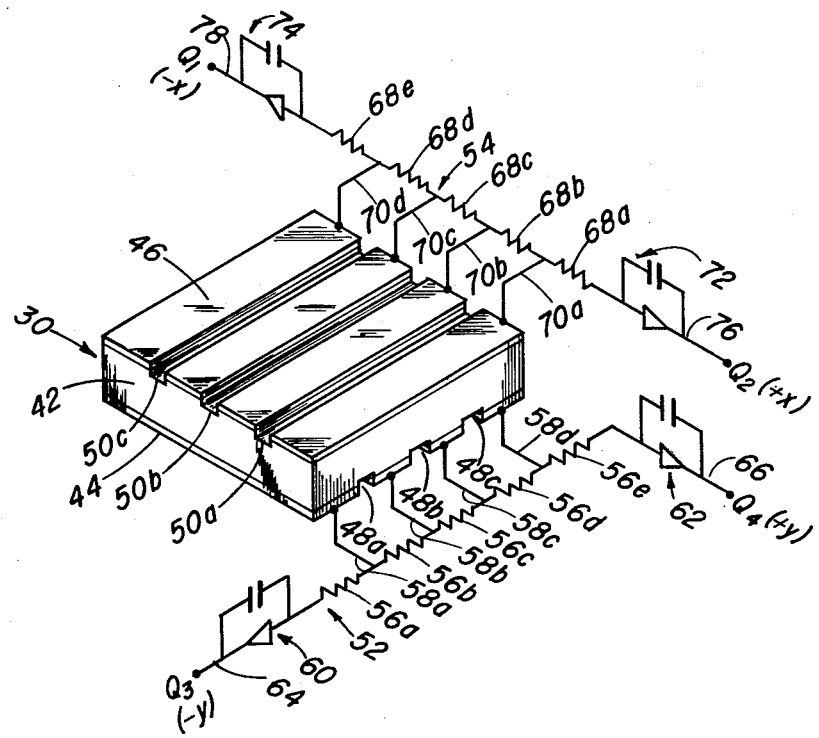
FIG. 2 is a pictorial representation of a solid state orthogonal strip high purity germanium detector incorporating a charge splitting resistor network in combination with preamplification electronics.

Looking to FIG. 2, an exaggerated pictorial representation of a portion of a single component detector 30 is revealed. Such gamma ray detectors are, in essence, a body of exceedingly high purity material as, for example, germanium, wherein a thick depletion region may be established by a high reserve bias so as to be sensitive to the impingement of ionizing radiation. Basically, such devices include, for example, a body of germanium having a relatively thick intrinsic, or near intrinisic, region with a donor or n+ surface-adjacent region on one major surface thereof and an acceptor or p+ region on the opposite major surface thereof. Accordingly, as shown in FIG. 2, a high purity gemanium region of such crystal, as at 42, serves as an intrinsic region between p-type semiconductor region contacts 44 and n-type semiconductor region contacts as at 46. The intrinsic region 42 of the p-i-n detector forms a region which is deplected of electrons and holes when a reverse bias is applied to the contacts. It should be understood that the detector component representation of FIG. 2 is idealized and simplified in the interest of facilitating the description thereof. As noted earlier, to achieve practical detector structures, a plurality of detector components are required which are so associated as to permit the generation of spatial image data which is accurate and reliable. In the embodiment shown, grooves as at 48a–48c are cut into the continuous p+-type region at one face of the detector to form strips of isolated p-type semiconductor material. On the opposite face of the detector, orthogonally disposed n-type semiconductor strips similarly are formed through the provision of grooves 50a – 50c. Configured having this geometry, the detector 30 generally is referred to as an orthogonal strip detector or an orthogonal strip array semiconductor detector. The electrode strips about each of the opposed surfaces of detector 30 of FIG. 1, respectively, are connected to external charge splitting impedance networks revealed generally at 52 and 54. Impedance network 52 is formed of serially coupled resistors 56a – 56e which, respectively, are tapped at their mutual interconnections by leads identified, respectively, at 58a – 58d extending, in turn, to the parallel strips. The opposed ends of network 52 terminate in preamplification stages 60 and 62, the respective outputs of which, at 64 and 66, provide spatial output data for insertion within the above-described Summation and Energy Level Derivation function 36 of FIG. 1 to provide one orthogonal or coordinate output, for instance, designated as a y-axis signal.

In similar fashion, impedance network 54 is comprised of a string of serially coupled resistors 68a–68e, the mutual interconnections of which are coupled with the electrode strips at surface 46, respectively, by leads 70a–70d. Additionally, preamplification stages as at 72 and 74 provide outputs, respectively, at lines 76 and 78 carrying spatial data or signals representative of image information along an x-axis or axis orthogonally disposed with respect to the output of network 52.

With the assertion of an appropriate bias over detector component 30, an imaging photon absorbed therewithin engenders ionization which, in turn, creates electron-hole pairs. The charge thusly produced is collected on the orthogonally disposed electrode strips by the bias voltage and such charge flows to the corresponding node of the resistor networks 52 and 54. Further, this charge divides in relation to the admittance of each path to the virtual ground input of the appropriate terminally disposed preamplification stage. Note that the distribution of charge across each of the impedance networks is one of proportionality, depending upon the position of interaction of a given photon with the crossing intersections of appropriate detector strips. While this proportion essentially remains constant for any given detector-impedance network structure, the value thereof may vary in accordance with the capacitance exhibited by the detector as well as the parameters of the impedance network associated therewith. Spatial informational signal outputs from such detectors also may be affected by the earlier noted aliasing phenomena wherein informational dysfunctions are evolved by virtue of the geometric relationship between the entrance channels of collimator 33 and the surface of the detector with which it is associated. Such phenomena, particularly, may be witnessed where a grooving technique, as illustrated in FIG. 2, is utilized to designate the discrete strips formed within the detector. The charge sensitive preamplification stage integrates the collected charge (a spatial determined percentage of the total charge directed to the network) to form a voltage pulse proportional to that charge value. Assigning charge value disignations $Q_1$ and $Q_2$, respectively, for the output line 64 and 66 of network 52, the above-noted Summation and Energy Level Derivation functions for spatial and energy data may be designated. In this regard, energy information is derived from the sum of the signals $Q_1$ and $Q_2$ or signals $Q_3$ and $Q_4$. This determines the total charge collected on one set of strips which is proportional to the energy of the photon detector interaction. Antisymmetrical summation is utilized to generate spatial information through subtractive logic. For example, the x-channel spatial signal is obtained by subtracting $Q_1$ from $Q_2$, and x-channel signal of zero volts corresponding to an interaction which occurred below the middle electrode strips. Similarly, the y-channel spatial signal is obtained by subtracting $Q_3$ from $Q_4$. The spatial channels of the imaging system use Gaussian-trapezoidal pulse shaping amplifiers, while the energy chan operating in conjunction with the Logic Control energy discrimination function described in connection with block 40, utilizes Gaussian pulse shaping and additive summing in carrying out requisite imaging control. As noted above, the operational environment of the detector 30 as well as the charge splitting resistor networks 52 and 54 is one within the cryogenic region of temperature for purposes of reducing Johnson noise phenomena and the like.

Figure 3:
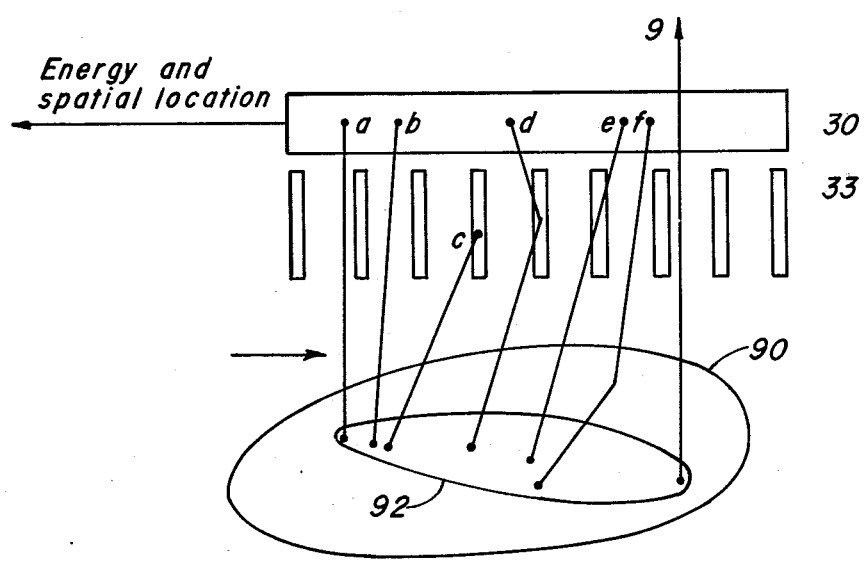
FIG. 3 is a schematic representation of a solid state orthogonal strip detector and associated collimator as such components relate to a radiation source situate within a region of clinical interest.

As a prelude to a more detailed consideration of the spatial resolution of gamma radiation impinging upon the entrance components of the gamma camera, some value may be gleaned from an examination more or less typical characteristecs of that impinging radiation. For instance, looking to FIG. 3, a portion of a patient's body under investigation is portrayed schematically at 90. Within this region 90 is shown a radioactively tagged region of interest 92, from which region the decay of radiotracer releases photons which penetrate and emit from the patient's body. These photons then are spatially selected by the collimator 33 and individually detected at detector 30 for ultimate participation in the evolution of an image display. The exemplary paths of seven such photons are diagrammed in the figure, as at a–g, for purposes of illustrating functions which the camera system is called upon to carry out. In this regard, the function of collimator 35 is to accept those photons which are traveling nearly perpendicular to the detector, inasmuch as such eminating rays provide true spatial image information. These photons are revealed at ray traces a and b, showing direct entry through the collimator 33 and appropriate interaction coupled with energy exchange within detector 30. Photon path c is a misdirected one inasmuch as it does not travel perpendicularly to the detector. Consequently, for appropriate image resolution such path represents false information which should be attenuated, as schematically portrayed. Scattering phenomena within collimator 33 itself or the penetration of the walls thereof allows "non-collimated" photons, i.e. ray traces d and e, to reach the detector. Photon path trace f represents Compton scattering in the patient's body. Such scattering reduces the photon energy but may so redirect the path direction such that the acceptance geometry of the camera, including collimator 33, permits the photon to be accepted as image information. Inasmuch as the detector 30 and its related electronics measure both the spatial location and energy of each photon admitted by the collimator, the imaging system still may reject such false information. For example, in the event of a Compton scattering of a photon either in the patient or collimator, the energy thereof may have been reduced sufficiently to be rejected by the energy discrimination window of the system. Photon path, g, represents a condition wherein detector 30 exhibits inefficient absorption characteristics such that that incident photon path, while representing true information, does not achieve a state of interaction with the detector. As is apparent from the foregoing, each of the thousands of full energy photons which are absorbed at detector 30 ultimately are displayed at their corresponding spatial location on an imaging device such as a cathode ray tube to form an image of the source distribution within region 92 of the patient.

Now considering the practical clinical aspects of such imaging, as noted earlier, it is necessary that the detector function of the gamma camera be capable of recording the imagewise distribution of a radiopharmaceutical as it extends over a region of practical extent, for instance, an active organ. Consequently, it is necessary that the detector function of the gamma camera be of size sufficient to accept photon information from as broad region as is possible. Inasmuch as the size of detector crystals inherently is limited by the techniques of its fabrication, it becomes necessary to conjoin a plurality of such crystal detectors in some manner wherein a broader region of radiation may be witnessed. More particularly, it currently is understood that the largest square shape detector that can be cut from available high purity germanium crystals or the like is one of about 3.7 centimeters per square side.

Figure 4:
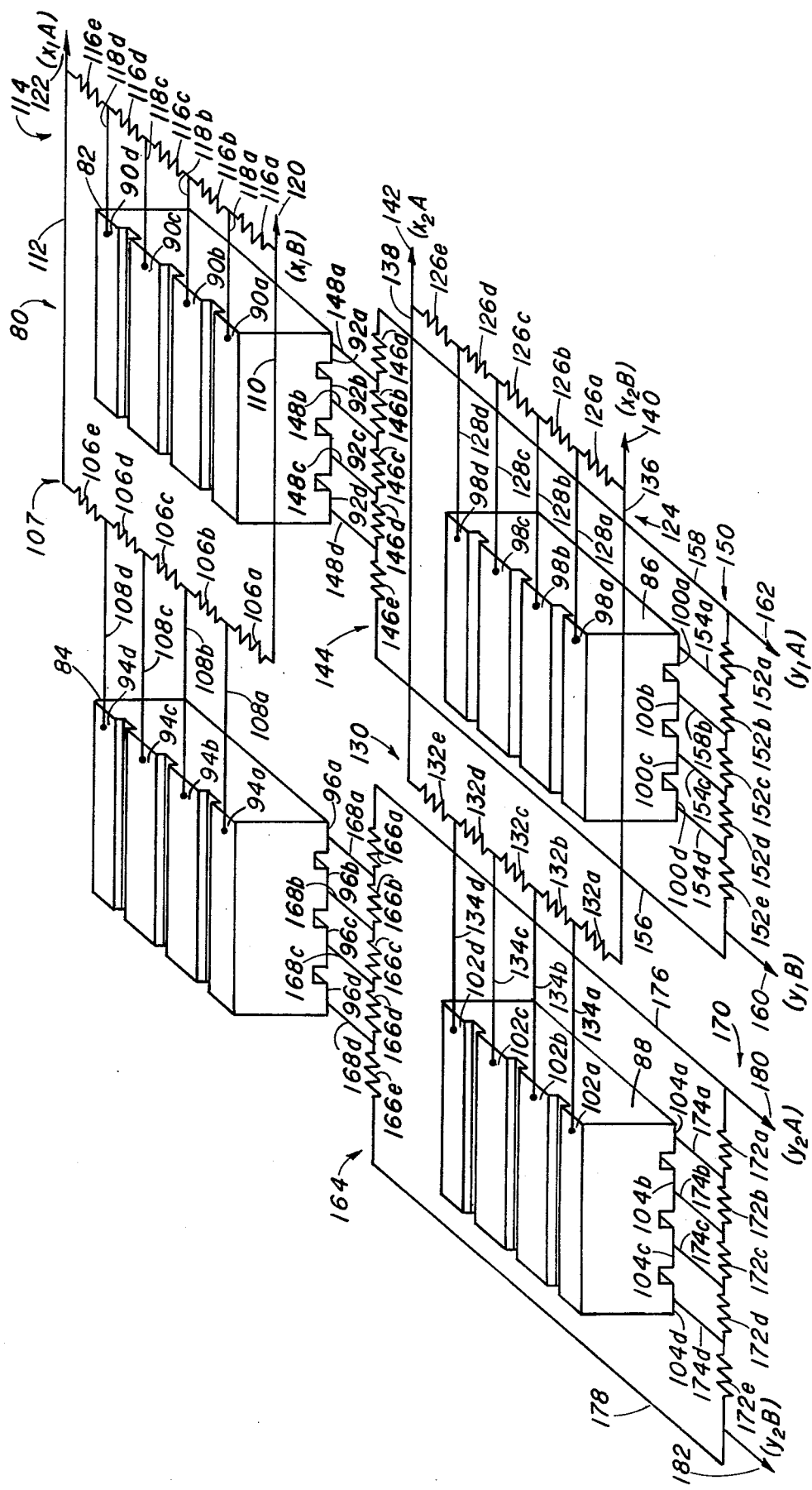
FIG. 4 is a pictorial and schematic representation of an array of detector components showing the interconnections thereof to form a composite detector according to the invention.

Referring now to FIG. 4, a composite detector formed as an array discrete detector components is revealed generally at 80. Illustrated in exploded fashion, the detector 80 is comprised of a plurality of detectors, four of which are shown at 82, 84, 86, and 88. Detectors 82 – 88 are dimensioned having mutually equivalent areas as are intended for acceptance of impinging radiation. This required equivalency serves to achieve an accurate ultimate image readout from the camera system. In the absence of such equivalency, distortion at such readout, exhibiting a discontinuity of image information, would result. The detector components illustrated are of the earlier-described orthogonal strip array variety, each strip thereof being defined by grooves. Note, in the regard, that detector component 82 is formed having strips 90a – 90d located at its upward surface and defined by grooves cut intermediate adjoining ones of said strips. The opposite face of detector component 82 similarly is formed having strips 92a – 90d defined by intermediately disposed grooves arranged orthogonally with respect to the grooves at the upper surface. Detector component 84 is identically fashioned having strips 94a–90d at its upwardly disposed surface and lower surface, orthogonally disposed strips 96a – 96d each strip being defined by intermediately formed grooves. Similarly, detector component 86 is formed having strips 98a – 98d at its upward surface defined by intermediately disposed grooves, while its lower surface similarly is formed having strips 100a – 100d defined by intermediately disposed grooves arranged orthogonally with respect to the grooves of the upward surface. Detector component 88 may be observed having strips 102a – 102d at its upward surface defined by intermediately designated grooves, while its lower surface is formed with strips 104a – 104d separated by intermediately disposed grooves arranged orthogonally to the grooves of the upward surface of the component.

Detector components 82 – 88 as well as similar components in later figures are illustrated expanded from one another for purposes of illustration only, It being understood that in an operational embodiment these components are internested together in as practical a manner as possible. To achieve an informational spatial and energy output from the discrete detector components which essentially is equivalent to that output which would be realized from a large detector of equivalent size, the strip arrays are functionally associated under a geometry which may be designated "row" and "column" in nature. In this regard, note that an impedance network, shown generally at 107, is associated with the strips 94a – 94d of detector component 84. This network incorporates discrete resistors 106a – 106e which are tapped at their common junctions by leads 108a – 108d extending, respectively, to strips 94a – 94d. Thus configures, network 107 closely resembles the impedance networks described herein in connection with FIG. 2. Note however, that output lines 110 and 112 of network 106 extend to and are coupled in parallel circuit relationship with the corresponding output of similar impedance network, identified generally at 114. Network 114 incorporates discrete resistors 116a – 116e which are tapped at their common interconnections by leads 118a – 118d. Leads 118a–118d, in turn respectively extend to strips 90a – 90d of detector component 82. Accordingly, the upwardly disposed surfaces of detector components 82 and 84 are identically associated with respective impedance networks 114 and 107, while the latter are interconnected in row fashion and in parallel circuit relationship to extend to principal output terminals, as are depicted generally at 120 and 122. It may be noted, that the information collected at these principal terminals represents one imaging spatial coordinate parameter of a select directional sense i.e. along a designated row.

Looking now to the functional interrelationship of detector components 86 and 88, a similar coordinate parameter direction or row-type informational collection network is revealed. In this regard, note that the impedance network, shown generally at 124, is configured comprising discrete resistors 126a – 126e, the points of common interconnection of which are coupled with respective leads 128a – 128d. Leads 128a – 128d, in turn, respectively, are connected with strips 98a – 98d at the upwardly disposed surface of detector component 86. Likewise, an impedance network, shown generally at 130 incorporating discrete resistors 132a – 132e, is associated with detector component 88 by leads 134a – 134d extending, respectively, from strips 102a – 102d to the points of common interconnection of the network discrete resistors 132a – 132e. Additionally, the output lines as at 136 and 138 of network 130 are connected in parallel circuit relationship with the output of network 124 to provide row readout termini, respectively, at 140 and 142. Here again, a row-type directional spatial coordinate parameter is provided at the upwardly disposed surface of the composite detector 80.

Looking now to the lower surfaces of the detector components, it may be observed that the orthogonally disposed strips of detector component 82 are associated with an impedance network identified generally at 144. Network 144 incorporates discrete resistors 146a – 146e which are coupled from their mutual interconnections by leads 148a – 148d, respectively, to strips 92a – 92d of detector 82. Similarly, the orthogonally disposed strips of detector component 86 are associated with an impedance network 150. In this regard, network 150 is formed of descrete resistors 152a – 152e which, in turn, are coupled, respectively, with strips 100a – 100d by leads 154a – 154d. The output of impedance network 144 is connected by leads 156 and 158 to the corresponding output of impedance network 150 to provide column directional coordinate parameter outputs, as at 160 and 162, which serve to collect all spatial information of the associated paired surfaces of detectors 82 and 86.

Looking to the lower surface of detector component 84, note that a network, designated generally at 164, incorporating discrete resistors 166a – 166e is functionally associated with strips 96a – 96d, respectively, by leads 168a – 168d.

In similar fashion, an impedance network, designated generally at 170, is associated with the orthogonally disposed strips 104a – 104d at the lower surface of detector component 88. Note that the network, incorporating discrete resistors 172a – 172e, is functionally associated with the array of strips 104a – 104d, respectively, by leads 174a – 174d. Networks 164 and 170 are electrically coupled in parallel circuit fashion by collector leads 176 and 178 extend to principal collection points or termini 180 and 182. Thus interconnected, the lower surfaces of detectors 84 and 88, are coupled in column readout fashion to provide another spatial coordinate parameter of direction parallel with the corresponding lower surface strip array readout arrangement of detector components 82 and 86.

With the row and column readout intercoupling of the detector components as shown in the figure, it may be observed that the capacitance exhibited by all discrete detector components, taken together, remains the same as if only a single detector were operating within a camera. Accordingly, the signal treating circuitry and logic of the camera, advantageously, may be designed to accommodate for the charge collection time constant of a single detector. Connection with the row and column readout for given spatial coordinate parameters is provided by more or less typical multiplexing input networks which then distribute collected spatial and energy signals into analyzing and distributing circuitry.

Such circuitry is described in more detail in connection with FIG. 6. However, it should be understood that, in a preferred embodiment, preamplification stages, as described in connection with FIG. 2, are coupled with each row readout point as at 120 and 122 or 140 and 144, as well as with each column readout, as at 160 and 162 and 180 and 182. Such preamplification stages generally are located within or near the cryogenic environment of the detector itself. The mounting of the contact leads between each of the networks and an associated strip array surface of a detector generally may be carried out by resort to biased contact configurations.

The composite detector arrangement or interrelated detector component mosaic also may be formed utilizing detector structures which incorporate surface disposed resistive layers to achieve spatially proportioned charge readout characteristics. Such as detector composite is revealed generally in FIG. 5 at 200. Referring to that figure, the composite detector, or portion thereof, 200, is shown to comprise four discrete detector components 202-208. The opposed surfaces of the detector components, which are situated generally normally to impinging radiation, are formed having a resistive character. This resistance is provided for instance, by so lightly doping the n-type surface as to achieve a region of resistive character, while, similarly, so lightly doping the opposite surface with a p-type acceptor as to achieve a surface resistive character thereat. The readout from these resistive surfaces is collected by conductive strips which, for the case of detector component 202, are shown on the upward surface at 210 and 212 and at the lower surface at 214 and 216. Conductive surfaces 210 – 216 may be deposited upon the detector component 202, for instance, by conventional evaporation techniques utilizing a highly conductive metal such as a noble metal, i.e. gold.

Concerning the techniques for developing the noted resistive regional character within the surfaces of detector components 202-208, mention may be made of the following publications:

XXI Owen, R. P., Awcock, M. L.. "One and Two Dimensional Position Sensing Semiconductor Detectors," IEEE, Trans. Nucl. Sci., Vol. N.S. - 15, June 1968, Page 290.

XXII Berninger, W. H., "Pulse Optical and Electron Beam excitation of Silicon Position Sensitive Detectors", IEEE, Trans. Nucl. Sci., Vol. V.S. 21, Page 374.

With the impingement of radiation upon detector component 202 and resultant development of an interaction therewithin, charge will be collected on the opposed surfaces, as discussed above, and will split proportionally at the impedance define surfaces and collect at the conductive strips 210 – 216. For the upwardly disposed surface, these charges then are collected along conduit 218, coupled with conductive strip 212, and conduit 220, coupled with conductive strip 210. The adjacently disposed detector 204 is fashioned in similar manner, the upward surface thereof incorporating a resistive surface layer or region formed in cooperation with conductive strips 220 and 222. The lower surface of detector component 204 is formed incorporating a similar resistive layer or region functionally associated with conductive strips 224 and 226. Note that the latter conductive strips are arranged orthogonally with respect to those at 220 and 222. Conductive strip 220 is coupled by a lead or conduit 228 to conductive strip 212 of the detector component 202, while conductive strip 222 is coupled by lead or conduit 230 to conductive strip 210 of detector 202. Thus interconnected, it will be apparent that any interaction occurring within detector component 204 will be "seen" as a charge division between strips 220 and 222, for one coordinate parameter, along leads 228 and 230 as well as output conduits 218 and 220. As is apparent, a desirable simplification of the structure of the composite detector is available with this form of row readout.

Looking to the adjacently disposed row of detector components 206 and 208, it may be noted that detector component 206 is formed incorporating resistive layers or regions in its opposed surfaces aligned for the acceptance of radiation and, additionally, incorporates conductive strips as at 232 and 234 at the extremities of its upward surface as well as orthogonally oriented conductive strips 236 and 238 about the extremities of its lowermost and oppositely disposed surfaces.

Identically structured component 208, similarly, is formed having resistive surfaces or regions arranged normally to the direction of radiation impingement. The surfaces also incorporate conductive strips, as at 240 and 242, at the upwardly disposed side and, at 244 and 246, orthogonally disposed at the lowermost surface.

Coupled in similar row-type fashion as detectors 202 and 204, the conductive strips of detectors 206 and 208 are directly electrically associated by leads 248 and 250. Note, in this regard, that lead 248 extends between conductive strips 240 and 232 while lead 250 extends between conductive strips 242 and 234. The output of that particular row at the upward surface of the composite detector is represented by leads 252 and 254.

A columnar interconnection of the detector components is provided between the orthogonally disposed conductive strips 214 and 216 of detector 202, respectively, as by leads 256 and 258, to similarly disposed conductive strips 236 and 238 of detector 206. The columnar readouts for the paired detector components are present at conduits 260 and 262 extending, respectively, from conductive strips 236 and 238.

In similar fashion, the columnar association of detector components 204 and 208 is provided by leads 264 and 266 which, respectively, extend between conductive strips 224 and 226 of detector 204 to corresponding conductive strips 244 and 246 of detector component 208. The readouts for the column association of detectors 204 and 208 are provided by conduits 268 and 270 extending, respectively, from conductive strips 244 and 246 of detector component 208.

As in the embodiment of FIG. 4, the output conduits 218, 220 and 252, 254 are of a "row" variety having a designated spatial coordinate parameter and are addressed to initial preamplification stages prior to their association with logic circuitry for deriving imaging information for that particular spatial coordinate. Similarly, the "columnar" outputs at conduits 260, 262 and 268, 270 are directed to preamplification stages, thence to appropriate circuitry for treating that spatial coordinate parameter. It will be understood, of course, that the number of detector components formed within a matrix or array thereof depends upon the field of view desired for a particular camera application as well as the practicalities for retaining such components under appropriate cryogenic temperature conditions during operation.

Figure 5:
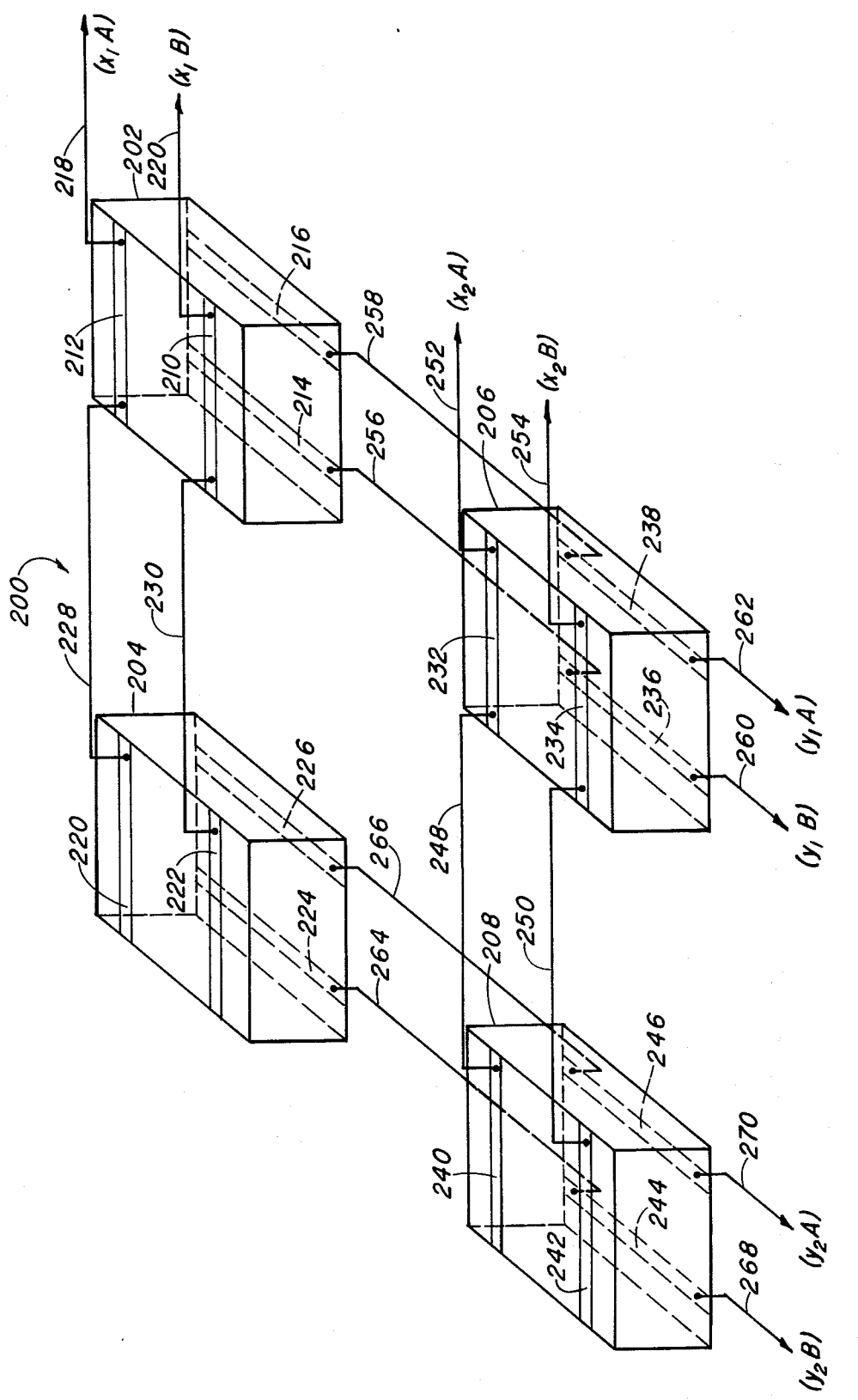
FIG. 5 is a schematic and pictorial representation of another array of detector components interconnected in accordance with the invention, the said components being formed having resistive surface regions combined with conductive strip readout elements.

The foregoing examination of the composite detector structures, represented in FIGS. 4 and 5, reveals certain consistent characteristics between the embodiments. For instance, as alluded to above, the effective areas presented to radiation impingment of the discrete detector components must be substantially equivalent, in order to avoid distortion in an ultimately developed image. Additionally, these components should be as closely nested as possible and aligned such that the spatial coordinate which may be designated for each surface evolves what has been termed as a "row-column" orientation. In the latter regard, an observation of this geometry shows that the leads interconnecting the impedance networks or the impedance structure i.e. at the surface region of the detector components, connect them directly, whether in the parallel-series connection of the embodiment of FIG. 4 or the interconnection of conductive strips shown in FIG. 5. Another aspect typifying the structure of the invention, reveals that any two adjacent surfaces of any two adjacent detector components exhibit spatial coordinate parameters of a common directional sense and, more particularly, two adjacent of the coplanar surfaces of any two adjacent detector components are disposed within a linearally oriented grouping arranged to exhibit a common spatial coordinate parameter directional sense. Because the composite detector embodiments shown in FIGS. 4 and 5 operate substantially in the same functional manner, their outputs are identified with the same spatial coordinate directional labels. For instance, outputs 122 and 120 of the embodiment of FIG. 4, respectively, are identified as $(X_1A)$ and $(X_1B)$; while the parallel row readouts, as at output points 142 and 140, respectively, are identified as $(X_2A)$ and $(X_2B)$. Similarly, the orthogonally disposed spatial coordinate parameters, as represented for instance, at outputs 162 and 160, respectively, are identified as $(Y_1A)$ and $(Y_1B)$. Next adjacent to that column of the composite detector, are the detectors whose outputs are represented at 180 and 182 and are identified, respectively, as $(Y_2A)$ and $(Y_2B)$. This same labeling procedure will be seen to be utilized in the composite detector embodiment of FIG. 5.

Figure 6:
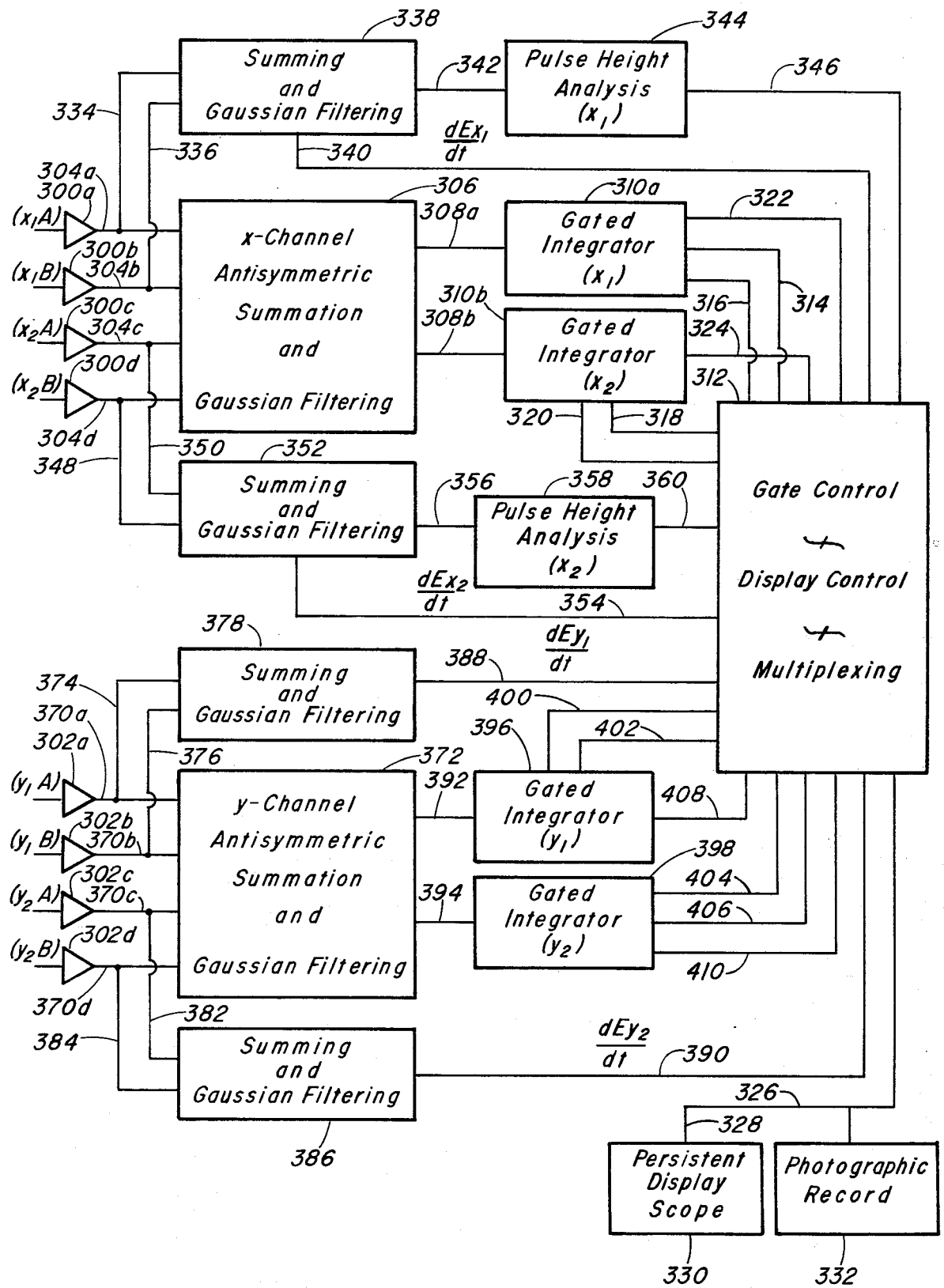
FIG. 6 is a block schematic representation of a control system for a gamma camera.

Turning now to FIG. 6, a schematic block diagram of a control system utilized in treating the above-identified output Turning now to FIG. 6, a schematic block diagram of a control system utilized in treating the above-identified output signals is revealed. Note in that figure, that the $x$ coordinate inputs, as above outlined, are shown arranged to address discrete preamplification stages $300a$ – $300d$, while the corresponding $x$ coordinate outputs are aligned to address preamplification stages $302a$ – $302d$. Generally, to accommodate for noise considerations, the preamplification stages $300a$ – $300d$ and $302a$ – $302d$ are incorporated within the cryogenic environment of housing 16 of the camera (FIG. 1). As is described in more detail in the above-reference application for U.S. patent Ser. No. 680,754, the $x$-channel coordinate inputs treated through preamplification stages $300a$ – $300d$ are, in turn, introduced along respective lines $304a$ – $304d$ to an Antisymmetric Summation and Gaussian Filtering function, represented at 306. This function serves to subtractively sum the inputs from each of the $x$ spatial coordinate channels, for instance, the signal at $(X_1A)$ is subtracted from that of $(X_1B)$. Following appropriate filtering and pulse shaping, as by a series of integrations, the output of block 306 is submitted along lines $308a$ and $308b$, respectively, to Gated Integrator functions $310a$ and $310b$. Within these functions, a trapezoidal filtering of the spatial signals is carried under a predesignated idealized integration time, generally selected as about one-eighth of the time constant characteristic of each of the discrete detector components. Control over gated integrators 310a and 310b emanates from a Gate Control, Display Control and Multiplexing function 312. In this regard, control from function 312 to gated integrator 310a is derived from lines 314 and 316, while similar control to Gated Integrator 310b is asserted through lines 318 and 320. The final integrated spatial x coordinate outputs of integrators 310a and 310b, respectively, are directed into a receiving network of Gate Control function 312 through lines 322 and 324. When accepted by the control circuit, the signals ultimately are asserted from function 312 through lines 326 and 328 to Persistent Display Scope 330 and Photographic Record 332.

The input signals at lines 304a and 304b, representing a linerally oriented grouping ($X_1A$) and ($X_1B$), are additionally directed, respectively, through lines 334 and 336 to a Summing and Gaussian Filtering function identified at block 338. Function 338 operates under a relatively extended time constant to additively sum the x-channel spatial signals as well as provide the noted filtering function. By carrying out an additive summing function, a signal representative of the energy value of a quantum of spatial information is derived. The value of this signal then may be utilized for purposes of determining whether or not the information which it represents is true or false in the sense of its ultimate participation in the image of a distribution of a radiopharmaceutical. A low level or preliminary evaluation of the signal is provided by tapping an initial stage of function 338 wherein the time derivative of the summed energy signal is generated. This derivative signal, identified as $dE_{x1}/dt$, is provided at line 340 for introduction to the control and multiplexing function at block 312. With such signal, the system commences an evaluation of the spatial signal, which evaluation includes a pulse height analysis of the summed signal received from line 342 at function block 344. The acceptance or rejection of the spatial signal is determined at block 344 and such determination is signalled to the display control networks of function 312, as from along line 346.

The same function is carried out for the ($X_2A$) - ($X_2B$) input signals, derived, respectively, at input lines 304c and 304d. In this regard, note that these input lines, respectively, are tapped by lines 348 and 350 which, in turn, lead to summing and Gaussian Filtering Function 352. As before, an initial stage of function 352 provides a time derivative output signal of the additively summed spatial signal, which is represented as $dE_{x2}/dt$, and is provided at line 354. As described in connection with the $X_1$ grouping above, this derivative signal is introduced to the display control and multiplexing networks of function 312 to provide a preliminary or low level analysis of the spatial information. Should the derivative signal evidence an appropriate signal level, the Gaussian filtered output of block 352 is directed through line 356 to pulse height analysis function 358. When the signal received therein is analyzed and found to fall within the appropriate window criteria evidencing appropriately true spatial information, it is passed along line 360 to control function 312 to enable a display of the $X_2$ coordinate parameter information.

The orthogonally disposed coordinate channel or y-channel information operates in substantially the same manner as the x-channel information treatment described above. For instance, the signal data derived at one column of the composite detector, as identified at ($Y_1A$) - ($Y_1B$), is introduced through respective preamplification stages 302a and 302b to lines 370a and 370b which, in turn, lead to a y-channel Antisymmetric Summation and Gaussian Filtering function 372. In like manner, the corresponding columnar derived spatial signals ($Y_2A$) - ($Y_2B$), respectively, are introduced through preamplification stages 302c and 302d to lines 370c and 370d which, in turn, lead to Summation and Filtering function 372. The $Y_1$ channel information initially is tapped, as by lines 374 and 376, connected, respectively, with lines 370a and 370b, to insert the coordinate signals to a Summing and Gaussian Filtering function 378. Similarly, lines 380 and 382, respectively tapping lines 380c and 380d, introduce the spatial $Y_2$ coordinate signals to a Summing and Gaussian Filtering function 386. Functions 378 and 386, operating in similar fashion as functions 338 and 352, serve the particular purpose of generating a time derivative valuation of the summed energy y-coordinate signal. In this regard, note that the output of function 378 at line 388 is labeled $dE_{y1}/dt$, while the output of function 386 at line 890 is identified as $dE_{y2}/dt$, both outputs leading to control function 312. The derivative signal from these functions is utilized in conjunction with coincidence circuits and the like at function 312 to provide an identification of that portion of the composite detector from which the spatial information signals were derived. In particular, the signal is utilized to identify the particular detector component responding by interaction with an impinging photon.

The filtered and subtractively summed signals from function 372 are introduced through lines 392 and 394, respectively, to Gated Integrator functions 396 and 398. Controlled under the above described time constant integrating interval through respective lines 400, 402 and 404, 406, integrators 396 and 398 perform a trapezoidal type filtering upon the spatial information pulses and deliver such treated information, respectively, along 408 and 410 to Multiplexing and Display Control function 312. Such information provides the y-coordinate channel inputs to readout functions 330 and 332.

An important aspect of the "row-column" interconnection of the discrete detector components resides in the realization of an effective reduction in that detector linear dimension over which resolution is evaluated. More specifically, an improvement is experienced in the resolution of the camera system which may be expressed by the equation:

$$\Delta x = \Delta E L / E,$$

where $\Delta x$, represents the spatial resolution in terms of distance; $\Delta E$, is absolute energy resolution; L, is length of a detector component, as measured parallel to the directional sense of an associated impedance network; and, E, represents the energy of an incident photon interacting with the detector. Within the right hand side of the equation above, the expression, $\Delta E/E$, is readily indentified as the fraction (or percentage) of energy resolution. Accordingly, any increase in the value of, L, directly and adversely affects that fraction. Where the detector components are not interconnected by the "row-column" technique, the value, L, in the expression above becomes 2L, effecting a doubling of the noted spatial resolution value to the detriment of final imaging. Another feature characteristic of a detector "row-column" interconnection resides in the presence of a common detector component for each combination of an associated row and column. Stated otherwise, a row or column configuration also may be designated as an orthogonally disposed linearly oriented grouping of charge collecting surfaces. Any interaction within any given common component will provide x- and y- designated coordinate output signals from the thus associated linear surface groupings.

Figure 7:
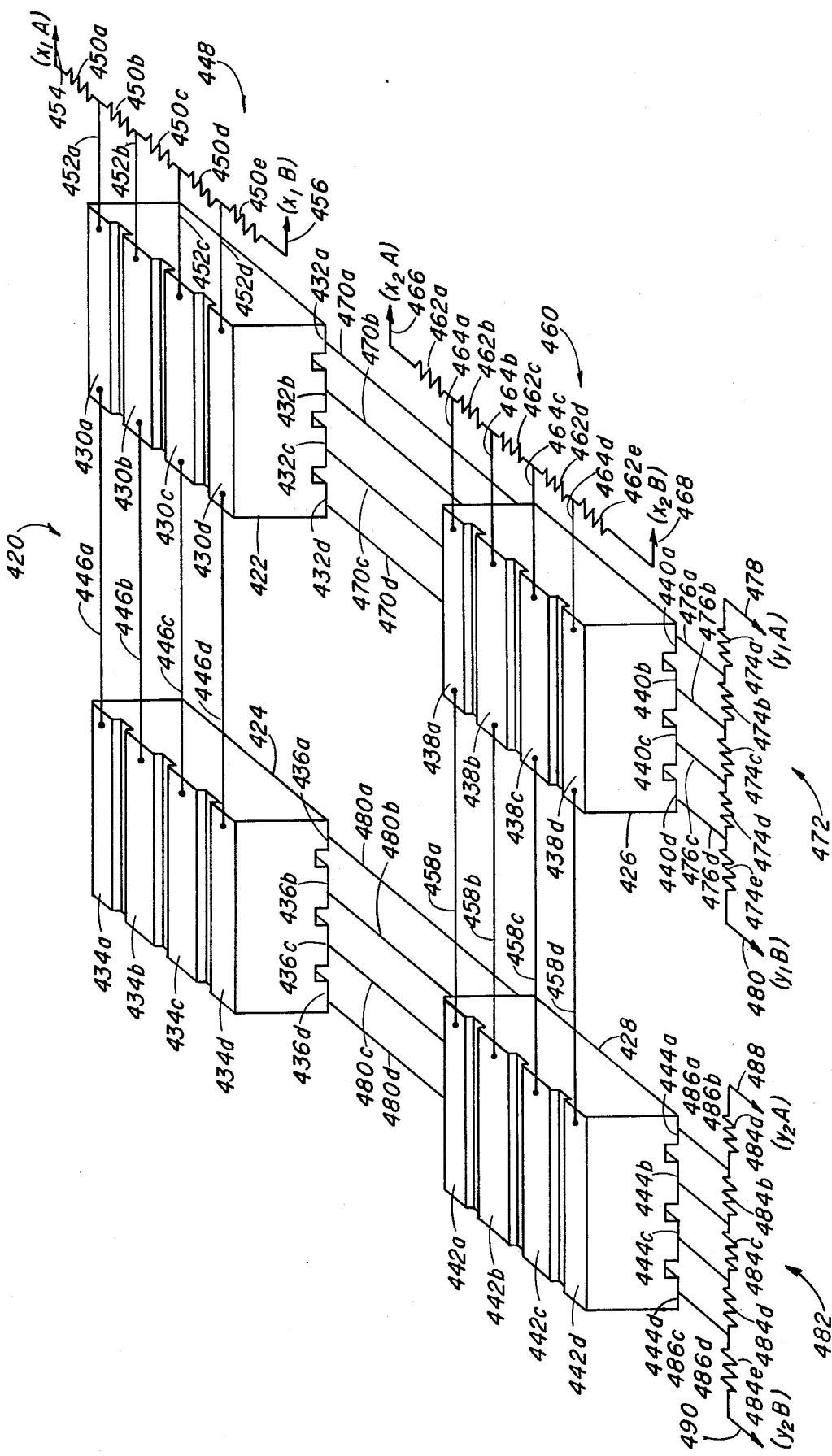
FIG. 7 is a pictorial and schematic representation of an array of detector components showing the interconnections thereof to form a composite detector in accordance with another embodiment of the invention.

A third embodiment of "row-column" interconnection of detector components exhibiting this spatial resolution advantage is revealed in FIG. 7. Referring to that figure, a composite detector formed as an array of discrete detector components is revealed generally at 420. As in the earlier-discussed embodiments detector 420 is shown in exploded fashion for purposes of clarity and comprises a plurality of detector components, four of which are shown at 422, 424, 426, and 428. Components 422-428 are dimentioned having mutually equivalent areas as are intended for acceptance of impinging radiation and, for illustrative purposes, are formed as of an orthogonal strip array variety, each strip thereof being defined by grooves formed within the detector surfaces. In this regard, detector 442 is formed having strips 430a - 430d defined by grooves cut within its upward surface. The opposite face of detector component 422 similarly is formed having strips 432a-432d defined by in intermediatly positioned grooves arranged orthogonally with respect to the grooves at the upper surface. Detector component 424 is identically fashioned, having strips 434a-434d formed at its upwardly disposed surface; and, at its lower surface, orthogonally disposed strips 436a 14 436d, adjacent said strips being defined by intermediatly formed grooves. Similarly, detector component 426 is formed having strips 438a-438d at its upward surface, adjacent ones of the strips being defined by intermediatly disposed grooves, while its lower surface similarly is formed having strips 440a-440d defined by intermediatly disposed grooves arranged orthogonally with respect to the grooves of the upward surface. Detector component 428 may be observed to have strips 442a-442d at its upward surface adjacent one of which are defined by intermediatly designated grooves, while its lower surface is formed with adjacently disposed strips 444a-444d separated by intermediatly disposed grooves arranged orthogonally to the grooves of the upward surface thereof.

In the instant embodiment, strips 434a-434d of detector component 424 are directly, electrically associated with corresponding row strips 430a-430d of component 422 by electrical leads respectively identified at 446a-446d. Note, that no impedance network is interposed intermediate the strip grouping as in the earlier embodiments. However, an impedance network, designated generally at 448, is associated with the termini of strips 430a-430d opposite the edges thereof coupled with electrical leads 446a - 446d. Network 448 comprises serially associated discrete resistors 450a-450e which are tapped at their common junctions by leads 452a-452d extending, respectively, to strips 430a-430d. The output, or readout points for the thus defined "row" of the composite detector assembly are represented at 454 and 456 and are provided the same respective output signal labeling, ($x_1$B), ($x_1$A), as are present in the corresponding "row" of the embodiments of FIGS. 4 and 5.

The corresponding upwardly disposed surfaces of components 426 and 428 are connected in similar fashion. For instance, strips 442a-442d are electrically coupled with strips 438a-438d by respective electrical leads 458a-458d. The "row" coupling thus provided is associated with an impedance network shown generally at 460. Network 460 is formed comprising serially associated discrete resistors 462a-462e which are tapped at their common interconnections by leads 464a-464d. Leads 464a-464d respectively, extennd to strips 438a-438d of detector 426. The principal output termini of the thus defined "row" are identified at 466 and 468 and respectively labeled ($x_1$B), ($x_1$A).

Looking now to the lower surfaces of the detector components, the orthogonally disposed strips of detector component 422 are electrically coupled as shown with the corresponding strips of detector component 426 by electrical leads 470a-470d. The thus coupled strip arrays of those detector components are associated in "columnar" fashion with an impedance network identified generally at 472. Network 472 comprises serially associated discrete resistors 474a-474e, the interconnections between which are connected as shown with strips 440a-440d of component 426 by leads respectively identified at 476a-476d. The readout termini for the thus defined "column" association of detectors 426 and 422 are present at 478 and 480 and identified, respectively, as ($y_1$A) and ($y_1$B).

The lower surfaces of detector components 424 and 428 similarly are associated in "columnar" readout fashion, strips 436a - 436d of the former being electrically connected through respective leads 480a-480d to strips 444a-444d of the latter. The thus established "columnar" readout is associated with an impedance network identified generally at 482 and comprising serially associated discrete resistors 484a-484e. Strips 444a-444d, respectively, are coupled with the interconnection of the resistors 484a-484e of network 482 by leads 486a-486d. As in the earlier embodiments, the principal readouts of the thus defined "columnar" detector component coupling are represented at 488 and 490 and are labeled, respectively, ($y_2$A) and ($y_2$B). From the foregoing description of the composite detector arrangement 420 it may be observed that the "row-column" association of the components thereof enjoys the noted spatial resolution advantages, however, the time constant characteristic thereof will reflect a higher capacity evaluation.

During performance, the composite detector 420 operates in the same manner as the control system of FIG. 6, which is described in conjunction with composite detector components 80 and 200 of respective FIGS. 4 and 5. For this reason, the noted labeling of the output of the "row and column" arrangement have remained consistent throughout all of the figures.

Since certain changes may be made in the above system and apparatus without departing from the scope of the invention herein involved, it is intended that all matter contained in the above description or shown in the accompanying drawings shall be intepreted as illustrative and not in a limiting sense.

We claim:

1. A composite solid state detector for use in deriving a display, by spatial coordinate information, of the distribution or radiation emanating from a source thereof situate within a region of interest, comprising:
a plurality of solid state detector components, each having a given surface arranged for exposure to impinging radiation and exhibiting discrete interactions therewith at given spatially definable locations;

said given surface of each said detector component and the surface disposed opposite and substantially parallel thereto, respectively, being associated with impedance means configured to provide, for each of said opposed surfaces, outputs for impedance defined signals relating the said given location of said interactions with one spatial coordinate parameter of one select directional sense;

said detector components being arranged to provide groupings of adjacently disposed ones of said given surfaces mutually linearly oriented to exhibit a common said directional sense of said spatial coordinate parameter; and means interconnecting at least two of said outputs associated with each of said surfaces within a given said grouping thereof for collecting said impedance defined signals deriving therefrom.

2. The composite solid state detector of claim 1 wherein said impedance means for each said detector component opposed surface is configured for providing said signals as charges of values corresponding with the said location of a said interaction along the said select directional sense of a said coordinate parameter associated with said surface.

3. The composite solid state detector of claim 1, wherein: the said opposed surfaces of a said detector component are configured to define arrays of mutually parallel strips, each said strip having a discrete area influenced by the occurrence of said interaction thereunder;

said impedance means for each said surface being present as a resistor network having opposed output terminals, the resistor components of a said network being arranged in correspondence with an associated said strip array to provide said impedance defined signals as charges at said opposed output terminals having values corresponding with the location of the strip influenced by a corresponding said interaction; and said interconnecting means is configured to associate, in parallel circuit relationship, the said output terminals of said resistor networks associated with a given said grouping of said surfaces having spatial coordinate parameters of mutually linear orientation.

4. The composite solid state detector of claim 3, in which the said array of strips of one said surface of a said detector component are orthogonally disposed with respect to the said array of strips of the said opposed surface oppositely disposed with respect thereto.

5. The composite solid state detector of claim 1, in which:

said impedance means is present as a surface-disposed region of predetermined resistance situate at a said detector component opposed surface and electrically coupled with a conductor means arranged upon said surface substantially at the edges of said component and in a direction transverse to said directional sense of said spatial coordinate parameters associated with said surface; and said interconnecting means is configured to associate, in series circuit relationship, the adjoining said conductor means situate at the associated surfaces of said adjacently disposed solid state detector components.

6. The composite solid state detector of claim 1, wherein:

said solid state detector components are disposed in substantial mutual adjacency; and said interconnecting means is configured to directly electrically connect the said impedance means outputs of said groupings of surfaces.

7. The composite solid state detector of claim 1, wherein:

said solid state detector components are disposed in substantial mutual adjacency; and any two adjacent said surfaces of each of any two said adjacent detector components exhibit spatial coordinate parameters of a common directional sense.

8. The composite solid state detector of claim 1, wherein:

said solid state detector components are disposed in substantial mutual adjacency;

said given surfaces of said detector components are disposed in substantially coplanar relationship; and two adjacent said coplanar surfaces of any two said adjacent detector components are disposed within a said linearly oriented grouping thereof.

9. The composite solid state detector of claim 8, wherein:

said impedance means for each said detector component opposed surface is configured for providing said signals as charges of values corresponding with the said location of a said interaction along the said select directional sense of a said coordinate parameter associated with said surface.

10. The composite solid state detector of claim 8, in which:

said impedance means is present as a surface-disposed region of predetermined resistance situate at a said detector component opposed surface and electrically coupled with conductor means arranged upon said surface substantially at the edges of said component and in a direction transverse to said directional sense of said spatial coordinate parameters associated with said surface; and said interconnecting means is configured to associate, in series circuit relationship, the adjoining said conductor means situate within the associated surfaces of said adjacently disposed solid state detector components.

11. The composite solid state detector of claim 8, wherein:

said solid state detector components are disposed in substantial mutual adjacency; and said interconnecting means is configured to directly electrically connect the said impedance outputs of said groupings of surfaces.

12. The composite solid state detector of claim 8, wherein:

said solid state detector components are formed of germanium.

13. A camera system for imaging the distribution of a source of gamma radiation situate within a region of interest, comprising:

a housing positionable a select distance from said region of interest at a location for receiving said radiation;

means collimating said received radiation;

a composite, solid state detector mounted within said housing in an orientation for receiving said collimated radiation, said detector including:

an array of solid state detector components, having given surfaces arranged in mutual, close adjacency to define a composite detector radiation acceptance plane exposable to incoming collimated radiation, said detector components exhibiting discrete interactions, at given spatial locations, with radiation impinging thereupon at said acceptance plane, said given surface of each said detector component and the surface thereof disposed opposite thereto, respectively, being operationally associated with impedance means, said impedance means being configured in correspondence with the extent of an associated said detector component surface and having outputs situate at two opposed peripheries of said associated surface for providing signals relating the location of a said interaction within said component to the respective locations of said outputs;

said detector components being arranged within said array to define spatially aligned discrete rows and orthogonally disposed columns of said surfaces and the said impedance means outputs associated therewith;

means interconnecting said impedance means outputs within each said discrete row in parallel circuit relationship to provide a signal collection output, means interconneting said impedance means outputs within each said discrete column in parallel circuit relationship to provide a column signal collection output; and means responsive to signals received from said row signal collection outputs and said column signal collection outputs for deriving an image corresponding with said interactions.

14. The camera system of claim 13, wherein said impedance means for each said detector component surface is configured for providing said signals as charges of values corresponding with the location of a said interaction with respect to said outputs.

15. The camera system of claim 13, in which the areas of each said detector component surface defining said acceptance plane are substantially mutually equivalent.

16. The camera system of claim 15, in which detector component surfaces defining said acceptance plane have substantially the same peripheral shape.

17. The camera system of claim 13, in which:

said given surface and said opposite surface of said detector components are configured having arrays of parallel strips, the detector regions encompassed thereby being responsive to a said interaction to derive a spatially defined charge; and said impedance means associated with each said surface is present as a charge splitting resistor network coupled between the said outputs thereof.

18. The camera system of claim 17, in which the said array of parallel strips at a said given surface of a said detector component are arranged orthogonally to the array of parallel strips at said surface opposite said given surface.

19. The camera system of claim 18, in which said detector components are formed of germanium and said strips are defined by grooves formed within said detector component surfaces.

20. The camera system of claim 13, in which said impedance means for each said detector component surface is present as a surface-disposed region of predetermined resistance, and said outputs associated therewith are present as conductive layers disposed at said opposed peripheries.

21. The camera system of claim 13, wherein:

said responsive means includes a preamplification stage coupled with each said row signal collection output and said column signal collection output.

22. The camera system of claim 21, wherein:

said detector components, said impedance means, and said preamplification stages are mounted within said housing within an environment adapted to achieve temperatures in the cryogenic region.

* * * * *